US009358324B2

United States Patent
Blanquer et al.

(10) Patent No.: US 9,358,324 B2
(45) Date of Patent: Jun. 7, 2016

(54) HYDROPHOBIC POLYMER FOR PRODUCING MEDICAL DEVICES VISIBLE IN MRI

(75) Inventors: Sebastien Blanquer, Pezenas (FR); Jean Coudane, Lattes (FR); Renaud De Tayrac, Nimes (FR); Xavier Garric, Montpellier (FR); Vincent Letouzey, Montpellier (FR); Olivier Guillaume, Javene (FR)

(73) Assignees: CENTRE NATIONAL DE LA RECHERCHE SCIENTIFIQUE, Paris (FR); UNIVERSITE DE MONTPELLIER 2, Montpellier (FR); UNIVERSITE DE MONTPELLIER 1, Montpelier (FR); CENTRE HOSPITALIER UNIVERSITAIRE DE NIMES, Nimes (FR)

( * ) Notice: Subject to any disclaimer, the term of this patent is extended or adjusted under 35 U.S.C. 154(b) by 1095 days.

(21) Appl. No.: 13/382,667

(22) PCT Filed: Jul. 7, 2010

(86) PCT No.: PCT/IB2010/053111
§ 371 (c)(1),
(2), (4) Date: Mar. 23, 2012

(87) PCT Pub. No.: WO2011/004332
PCT Pub. Date: Jan. 13, 2011

(65) Prior Publication Data
US 2012/0178872 A1    Jul. 12, 2012

(30) Foreign Application Priority Data
Jul. 7, 2009  (FR) ...................................... 09 54690

(51) Int. Cl.
*A61K 49/12*   (2006.01)
*A61L 27/50*   (2006.01)
(Continued)

(52) U.S. Cl.
CPC ............... *A61L 27/50* (2013.01); *A61K 49/128* (2013.01); *A61L 27/16* (2013.01); *A61L 29/041* (2013.01);
(Continued)

(58) Field of Classification Search
CPC ............ C08F 8/42; C08F 20/14; C08F 20/16; C08G 18/4266–18/4283; C08G 85/002; C08G 85/004; C08G 2230/00; A61K 49/128
See application file for complete search history.

(56) References Cited

FOREIGN PATENT DOCUMENTS

| WO | 99 60920 | 12/1999 | |
|---|---|---|---|
| WO | 03 045457 | 6/2003 | |
| WO | WO 2010048268 A2 * | 4/2010 | ........... A61K 49/128 |

OTHER PUBLICATIONS

E. I. Vargha-Butler et al., "Wettability of biodegradable surfaces", Colloid Polym. Sci. 2001, 279, 1160-1168.*

(Continued)

*Primary Examiner* — Richard A Huhn
(74) *Attorney, Agent, or Firm* — Oblon, McClelland, Maier & Neustadt, L.L.P

(57) ABSTRACT

The present invention relates to a hydrophobic polymer used in particular to produce and/or coat medical devices, in particular implantable medical devices, that are visible in magnetic resonance imaging, characterized in that it comprises at least one monomer unit on which is grafted a chelating ligand of a paramagnetic ion complexed with such a paramagnetic ion, said monomer unit having at least one carbonyl group, said monomer unit comprising, prior to grafting, at least one hydrogen atom in the α position of said at least one carbonyl group, and said grafting of the chelating ligand taking place in the area of said at least one hydrogen atom in the α position of said at least one carbonyl group.

21 Claims, 5 Drawing Sheets

(51) Int. Cl.
| | |
|---|---|
| *A61L 27/16* | (2006.01) |
| *A61L 29/04* | (2006.01) |
| *A61L 31/04* | (2006.01) |
| *C08F 8/30* | (2006.01) |
| *A61L 29/18* | (2006.01) |
| *A61L 31/18* | (2006.01) |
| *C08F 20/14* | (2006.01) |
| *C08F 8/42* | (2006.01) |
| *C08G 18/42* | (2006.01) |
| *C08F 20/16* | (2006.01) |

(52) U.S. Cl.
CPC ............... *A61L 29/18* (2013.01); *A61L 31/048* (2013.01); *A61L 31/18* (2013.01); *C08F 8/30* (2013.01); *C08F 8/42* (2013.01); *C08F 20/14* (2013.01); *C08F 20/16* (2013.01); *C08G 18/4266* (2013.01); *C08G 18/4269* (2013.01); *C08G 18/4272* (2013.01); *C08G 18/4275* (2013.01)

(56) References Cited

OTHER PUBLICATIONS

J. A. P. Arias, "Synthesis, characterization and biomedical applications of microbial polymalic and polyglutamic acids derivatives." Thesis, Polytechnic University of Catalonia. Feb. 2008.*

Riva, R. et al., "Combination of Ring-Opening Polymerization and "Click Chemistry": Toward Functionalization and Grafting of Poly(ε-caprolactone)", Macromolecules 2007, 40, 796-803.*

Nottelet, B. et al., "Synthesis of an X-ray opaque biodegradable copolyester by chemical modification of poly (ε-caprolactone)", Biomaterials 2006, 27(28), 4948-4954.*

U.S. Appl. No. 14/364,007, filed Jun. 9, 2014, Coudane, et al.

Zhang, G., et al., "Micelles Based on Biodegradable Poly(L-glutamic acid)-b-Polyactide with Paramagnetic Gd Ions Chelated to the Shell Layer as a Potential Nanoscale MRI—Visible Delivery System," Biomacromolecules, vol. 9, pp. 36-42, (2008).

Sieving, P.F., et al., "Preparation and Characterization of Paramagnetic Polychelates and Their Protein Conjugates," Bioconjugate Chemistry, vol. 1, pp. 65-71, (1990).

Rebizak, R., "Polymeric Conjugates of $Gd^{3+}$-Diethylenetriaminepentaacetic Acid and Dextran. 2. Influence of Spacer Arm Length and Conjugate Molecular Mass on the Paramagnetic Properties and Some Biological Parameters," Bioconjugate Chemistry, vol. 9, pp. 94-99, (1998).

Ponsart, S., et al., "A Novel Route to Poly(E-carprolactone)-Based Copolymers via Anionic Derivatization," Biomacromolecules, vol. 1, pp. 275-281, (2000).

International Search Report Issued Sep. 29, 2010 in PCT/IB10/53111 Filed Jul. 7, 2010.

* cited by examiner

Figure 4:
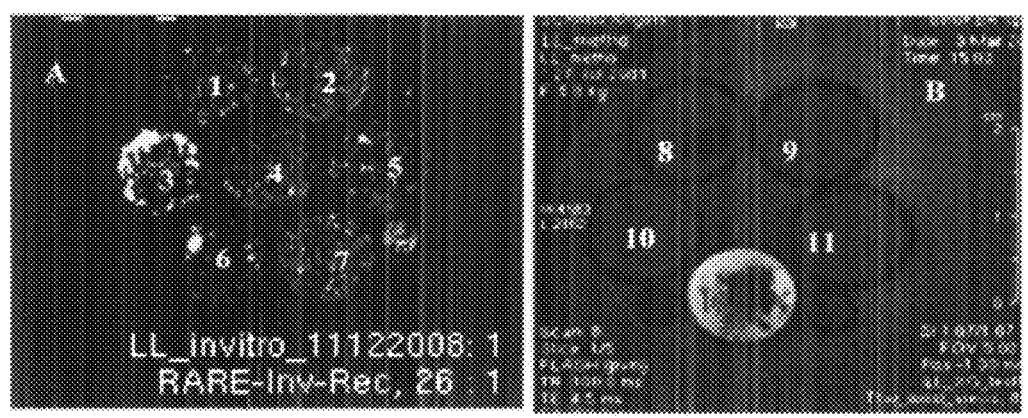

Fig. 4-A          Fig. 4-B

HYDROPHOBIC POLYMER FOR PRODUCING MEDICAL DEVICES VISIBLE IN MRI

This application is a National Stage of PCT/IB10/053111 filed Jul. 7, 2010 and claims the benefit of FR 09 54690 filed Jul. 7, 2009.

The present invention relates to the field of medical devices, notably which are implantable and are visible in magnetic resonance imaging.

The present invention relates more particularly to a novel polymer, having the property of being hydrophobic and insoluble in biological fluids, which can be used for making and/or coating medical devices, notably that are implantable, and are visible temporarily or permanently in magnetic resonance imaging.

The invention further relates to a method of preparation of said polymer and a method of preparation of a medical device, notably that is implantable, and detectable in magnetic resonance imaging, comprising said polymer in its bulk and/or as a coating.

The present invention finally relates to the resultant medical device, notably which is implantable.

Magnetic resonance imaging (MRI) is a medical imaging tool that makes it possible to obtain images of the human body owing to the presence of hydrogen atoms. In order to increase the intensity of the signal and the quality of the images obtained, a great many contrast agents are used, most of which are soluble in biological fluids, permitting better subsequent visualization in the organism.

However, MRI does not make it possible to visualize a great majority of polymer-based prostheses or medical devices that are implanted in the body with the aim of alleviating certain pathologies, and consequently monitor the fate of the latter in the organism.

Now, there is a need to be able to monitor the fate of these prostheses or implanted medical devices to evaluate the quality and durability of fixation for example, cellular integration, as well as any degradation of the prosthesis.

An implantable medical device is known from document WO 03/045457, comprising a substrate and a hydrogel polymer coating said substrate at least on a portion of the surface of said substrate, in which the hydrogel polymer is able to make said medical device visible in magnetic resonance imaging, once said device is implanted in a patient.

However, the hydrogel polymer is hydrophilic so that the detectable species trapped on said hydrogel polymer are not bound permanently to the medical device, which therefore cannot be visible long-term, once it is implanted.

Contrast agents for use in magnetic resonance imaging, comprising chelating agents bound to polysaccharides, are also known from document U.S. Pat. No. 4,822,594.

However, these are hydrophilic compounds. Moreover, grafting between the chelating agents and the polysaccharides takes place by formation of an ester bond resulting from the reaction of a —COOH or carbonyl group of the chelating agent directly with a hydroxyl or —OH group of the saccharide.

Thus, the position of the graft according to the present invention, as presented below, differs from that employed in this document.

Moreover, from document WO 99/60920, coatings are known that are able to emit signals detectable by magnetic resonance owing to the presence of paramagnetic metal ions that can be used for coating medical devices during diagnostic or therapeutic processes using magnetic resonance imaging, such as endovascular therapy.

However, the method described has major drawbacks, notably with respect to industrial application in that, firstly, it employs a step in a plasma reactor for pretreating the surface. As described in the examples in said document, polyethylene surfaces are first treated with plasma based on hydrazine, giving free $NH_2$ groups, prior to grafting of the complexing agent comprising the paramagnetic metal.

Moreover, this method also has the drawback that it makes it difficult to determine the quantity of paramagnetic ions, as the plasma treatment does not allow accurate evaluation of the number of free $NH_2$ groups capable of reacting and being bound to the complexing agent.

There is therefore a need to find hydrophobic polymers that are visible in magnetic resonance imaging and can be used either in the bulk or on the surface of implantable medical devices, the associated method of preparing said polymers being simple, easy to carry out and/or making it possible to control the quantity of paramagnetic ions detectable on said medical devices.

According to a first aspect, the present invention relates to a hydrophobic polymer, notably useful for making and/or coating medical devices, notably that are implantable, visible in magnetic resonance imaging, more particularly permanently, characterized in that it comprises at least one monomer unit, on which a ligand is grafted that chelates a paramagnetic ion, complexed with said paramagnetic ion, said monomer unit possessing at least one carbonyl group, said monomer unit comprising, prior to grafting, at least one hydrogen atom in the $\alpha$ position of said at least one carbonyl group and said grafting of the chelating ligand taking place at the level of said at least one hydrogen atom in the $\alpha$ position of said at least one carbonyl group.

According to another of its aspects, the present invention relates to a hydrophobic polymer, notably useful for making and/or coating medical devices, notably that are implantable, visible in magnetic resonance imaging, more particularly permanently, characterized in that it comprises at least one monomer unit, on which a ligand is grafted that chelates a paramagnetic ion, complexed with said paramagnetic ion, said monomer unit possessing at least one carbonyl group and said monomer unit comprising, prior to grafting, at least one hydrogen atom in the $\alpha$ position of said at least one carbonyl group.

It also relates to a method of preparing said polymer as defined above, comprising (i) at least one step of activation of a hydrophobic polymer comprising at least one monomer unit possessing at least one carbonyl group and comprising at least one hydrogen atom in the $\alpha$ position of said at least one carbonyl group to form a polymer chain having at least one monomer unit bearing a carbanion by elimination of the proton located on the carbon in the $\alpha$ position of said at least one carbonyl group, (ii) at least one step of grafting on said polymer having at least one monomer unit bearing a carbanion with a chelating ligand of a paramagnetic ion, and (iii) at least one step of complexation of the paramagnetic ion with the chelating agent, for example by dissolution of the polymer obtained in the preceding step in a solvent comprising at least one paramagnetic ion.

It also relates to a medical device, characterized in that it comprises at least one polymer as defined above in its bulk and/or as a coating and/or as a marker, notably for the purpose of traceability as described below.

The invention also relates to a method of preparing a medical device, notably that is implantable and is detectable in magnetic resonance imaging, characterized in that it comprises at least one step of coating with a polymer as defined above, notably by dipping or by spraying, in a solution comprising said polymer according to the invention.

In the context of the present invention, the following definitions are used:

- comprise the polymer "in its bulk" means that the object in question comprises said polymer within it, and for example consists essentially or partially of said polymer,
- the term "polymer chain" denotes a macromolecule or a portion of a macromolecule having a linear or branched sequence of consecutive units located between two limiting consecutive units, each of which can be an end group, a branching point or a characteristic feature of the macromolecule,
- the term "main polymer chain" denotes the linear portion of the polymer chain as defined above,
- the term "monomer" encompasses a molecule capable of being converted to a polymer by combining with itself or with other molecules of the same type,
- a "monomer unit" or "monomeric unit" denotes the smallest constituent unit, repetition of which leads to a regular macromolecule,
- a material that is "degradable hydrolytically" is a material that degrades in the presence of water following breaking of the ester bond by hydrolysis and for which there is proof that the products of degradation of the material have number-average molecular weights that are lower than the number-average molecular weights of the polymer chains of the starting material.
- a "bioabsorbable" or "absorbable" material is a material that degrades enzymatically or hydrolytically and for which there is proof that the products of degradation are integrated in biomass and/or are eliminated from the body by metabolization or renal filtration,
- "block" is a portion of a macromolecule comprising several identical or different constituent units, which possess at least one characteristic feature of constitution or of configuration, enabling it to be distinguished from the portions adjacent to it,
- the terms "complexing agent of a paramagnetic ion", "chelating agent of a paramagnetic ion" or "chelating ligand of a paramagnetic ion" are equivalent,
- the terms "between . . . and . . . " and "vary from . . . to . . . " signify that the limits of the range are included,
- "hydrophobic polymer" means a polymer with a measured contact angle between 40 and 180° and more preferably between 50 and 150°, for example according to the measurement protocol described in detail below.

In other words, the polymers according to the invention are insoluble in biological fluids.

Protocol for Measuring a Contact Angle

The contact angle can be measured with a tensiometer, for example KRUSS K100 sold by the company KRUSS.

According to Wihelmy's method, a clean, dry microscope slide is immersed in a solution of substituted polymer, with a concentration of 5 g/L dissolved in tetrahydrofuran (THF), corresponding to an immersion of 1 cm in water, said operation being carried out at 20° C.

The tensiometer measures the surface tension between the water and the polymer-coated slide, and calculates the resultant contact angle with water.

Novel Hydrophobic Polymers

The hydrophobic polymer according to the present invention is characterized in that it comprises at least one monomer unit on which a chelating ligand of a paramagnetic ion complexed with said paramagnetic ion is grafted, said monomer unit possessing at least one carbonyl group, and notably 1 to 3, and said monomer unit comprising, prior to grafting, at least one hydrogen atom in the α position of said at least one carbonyl group.

The invention relates to hydrophobic polymers as defined above that can have varied degradation profiles. In other words, depending on the nature of the polymer envisaged, as is detailed below, it may or may not be bioabsorbable or hydrolytically degradable. This property can thus be modulated easily depending on the application envisaged, which constitutes one of the advantages of the present invention. Advantageously, this property can be evaluated using the following degradation test.

Degradation Test

This test makes it possible to determine whether a polymer is bioabsorbable or hydrolytically degradable according to the definition given above. This test consists of investigating the variation, for example by size exclusion chromatography, of the number-average molecular weights in conditions imitating a physiological situation (PBS buffer at pH 7.4, mechanical stirring at 37° C.).

The percentage decrease in number-average molecular weight at different times is expressed by the following equation:

$$\% = \frac{\text{number-average molecular weight at } T_0 - \text{number-average molecular weight at } T}{\text{number-average molecular weight at } T_0}$$

As a guide, according to the present invention:

- for a time T=2 months, the percentage decrease in the number-average molecular weight can be between 0 and 50%, preferably between 0 and 25%.
- for a time T=6 months, the percentage decrease in the number-average molecular weight can be between 0 and 75%, preferably between 5 and 50%.
- for a time T=1 year, the percentage decrease in the number-average molecular weight can be between 5 and 100%, preferably between 10 and 80%.
- for a time T=2 years, the percentage decrease in the number-average molecular weight can be between 10 and 100%, preferably between 20 and 90%.

An illustration of application of the test is given in the following examples for a polymer according to the present invention.

Starting Polymer

The polymer chains that can give rise to the polymers according to the present invention are described below.

According to one variant of the invention, the monomer unit possessing at least one carbonyl group, and comprising at least one hydrogen atom in the α position of said carbonyl group, comprises from 2 to 12 carbon atoms, in particular from 2 to 7 carbon atoms.

According to another variant, the monomer unit has a single carbonyl group.

According to a first embodiment, the carbonyl group is located outside of the main polymer chain. As examples of such a polymer, we may notably mention the polyacrylates, consisting wholly or partly of identical or different monomer units, each of said units having the following formula (I):

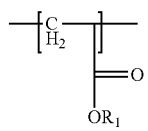
(I)

in which $R_1$ represents a $(C_1-C_{12})$alkyl group or a $(C_1-C_8)$ cycloalkyl group optionally substituted with a $(C_1-C_4)$alkyl group.

The polyacrylates are formed from acrylate monomers.

Among said acrylate monomers, we may mention in particular butyl acrylate, 2-ethylhexyl acrylate, methyl acrylate and ethyl acrylate.

These polymers possess the property of being regarded as nonabsorbable and not degradable hydrolytically. In other words, they are able to remain intact in the human body and do not degrade in contact with the biological environment.

In general, the polyacrylates of formula (I) can be obtained by polymerization of acrylate monomers defined above.

According to a second embodiment, the carbonyl group is located in the main polymer chain. As examples of this embodiment, we may mention in particular the polyester polymers consisting wholly or partly of identical or different monomer units, each of said units having the following formula (II):

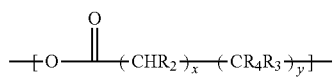
(II)

in which:
$R_2$, $R_3$ and $R_4$ independently represent a hydrogen atom, a $(C_1-C_{12})$alkyl group or a $(C_1-C_8)$cycloalkyl group optionally substituted with a $(C_1-C_{12})$alkyl group,
x represents an integer between 0 and 12, for example between 0 and 6, and
y represents an integer between 0 and 8, for example between 0 and 6, it being understood that x and y are not zero simultaneously.

In general, the polyesters of formula (II) can be obtained:
a) by polycondensation of a hydroxy acid on itself, or
b) by lactone ring-opening polymerization.

Among these polymers comprising monomer units of formula (II), we may notably mention the polyesters consisting wholly or partly of identical or different monomer units, each of the units having the following formula (III)

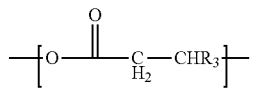
(III)

in which $R_3$ represents a $(C_1-C_{12})$alkyl group.

Among the monomers that can be used for preparing polyesters, we may notably mention hydroxybutyric acid, hydroxyvaleric acid, hydroxyhexanoic acid and hydroxyoctanoic acid.

The following table shows the correspondence between the meaning of the $R_3$ group and the full name of the polymer of formula (III).

| $R_3$ | Name of polymer |
|---|---|
| $CH_3$ | Polyhydroxybutyrate (PHB) |
| $C_2H_5$ | Polyhydroxyvalerate (PHV) |
| $C_3H_6$ | Polyhydroxyhexanoate (PHHx) |
| $C_5H_8$ | Polyhydroxyoctanoate (PHO) |

As an illustration of other polyesters comprising monomer units of formula (II), we may mention the polyesters obtained by opening of lactone rings of formula (IV)

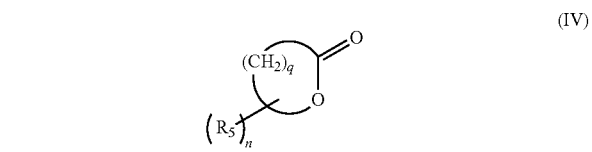
(IV)

in which:
q represents an integer that can vary between 2 and 9,
$R_5$ represents a $(C_1-C_{12})$ alkyl group, and
n is an integer between 0 and 2, it being understood that when n is equal to 2, the two $R_5$ groups not only can be different but also can be located on the same or on two different carbon atoms.

When q is equal to 5 and n is equal to 0, it is caprolactone or $\epsilon$-caprolactone.

The polyesters thus obtained are polycaprolactone or poly($\epsilon$-caprolactone). Among the lactones of formula (IV) that can be suitable for the present invention, we may further mention $\delta$-valerolactone; $\gamma$-butyrolactone; $\epsilon$-decalactone, pivalolactone and diethylpropiolactone.

As an illustration of other polyesters comprising monomer units of formula (II), we may mention the polymers of lactic acid (PLA) consisting wholly or partly of identical or different monomer units, each of said units having the following formula:

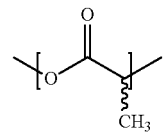

Generally the polymers of lactic acid are obtained from the lactide monomer, for example by ring-opening polymerization or from lactic acid or from derivatives of lactic acid by polycondensation. Owing to the chiral nature of lactic acid, there are poly-L-lactide (PLLA) and poly-D-lactide (PDLA), poly(D,L lactide), poly-meso-lactide and all the stereoisomers that form part of the polymers according to the present invention.

As an illustration of yet other polyesters of formula (II), we may mention the polymers of glycolic acid or poly(glycolide) consisting wholly or partly of identical or different monomer units, each of said units having the following formula

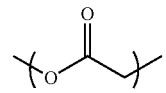

Among the polyesters comprising monomer units of formula (II) usable in the context of the invention, we may also mention the homopolymers and copolymers of p-dioxanone (1,4-dioxan-2-one); 1,4-dioxepan-2-one (including its 1,5, 8,1 dimers 2-tetraoxacyclotetradecane-7,14-dione), 1,4-dioxepan-5-one; 1,5-dioxepan-2-one; 6,6-dimethyl-1; 4-dioxan-2-one; 2,5-diketomorpholine; 3-methyl-1,4-dioxane-2,5-dione; 3,3-diethyl-1,4-dioxan-2,5-dione; 6,6-dimethyl-dioxepan-2-one and polymer mixtures thereof.

According to one of its aspects, the present invention relates to a hydrophobic polymer notably useful for making and/or coating medical devices, notably implantable, and visible in magnetic resonance imaging, characterized in that it comprises at least one monomer unit on which a chelating ligand of a paramagnetic ion complexed with said paramagnetic ion is grafted, said monomer unit possessing at least one carbonyl group and said monomer unit comprising, prior to grafting, at least one hydrogen atom in the α position of a carbonyl group, characterized in that it results from the polymerization of at least one monomer selected from hydroxybutyric acid, hydroxyvaleric acid, hydroxyhexanoic acid and hydroxyoctanoic acid; δ-valerolactone; γ-butyrolactone; ε-decalactone; pivalolactone; diethylpropriolactone; glycolic acid; p-dioxanone (1,4-dioxan-2-one); 1,4-dioxepan-2-one; 1,4-dioxepan-5-one; 1,5-dioxepan-2-one; 6,6-dimethyl-1; 4-dioxan-2-one; 2,5-diketomorpholine; 3-methyl-1,4-dioxane-2,5-dione; 3,3-diethyl-1,4-dioxan-2,5-dione; 6,6-dimethyl-dioxepan-2-one and mixtures thereof.

The polyesters of formula (II) are regarded as absorbable or degradable hydrolytically but over the long term. Thus, according to the degradation test described above, the variations in number-average molecular weight are observable in a period between 1 week and 10 years.

In actual fact, depending on the nature of the polyester, absorption can take from 1 month to 10 years. The present invention relates more particularly to the polyesters having an absorption time measured according to the protocol presented above of more than 1 month, or even 6 months.

As other polymers possessing a carbonyl group in the main polymer chain, we may also mention polyetherketones and polyamidoesters.

In the context of the present invention:
a carbonyl group means a divalent —CO— group;
(Ct-Cz) where t and z can take values from 2 to 12, means
  a carbon-containing unit that can have from t to z carbon atoms, for example ($C_2$-$C_3$) means a carbon-containing unit that can have from 2 to 3 carbon atoms;
an alkyl group is a saturated, linear or branched aliphatic group. As examples, we may mention the methyl, ethyl, propyl, isopropyl, butyl, isobutyl, tertbutyl, pentyl groups, etc.; and
a cycloalkyl group is a cyclic alkyl group. As examples, we may mention the cyclopropyl, cyclobutyl, cyclopentyl, cyclohexyl groups, etc.

According to a particular embodiment, the lactide, glycolide and ε-caprolactone homopolymers and copolymers are used as starting polymer.

According to an even more particular embodiment, the polymer usable in the context of the present invention is a homopolymer or a copolymer of ε-caprolactone, and more particularly a homopolymer of ε-caprolactone, in particular of number-average molecular weight between 5000 and 500 000, in particular between 5000 and 100 000.

In the sense of the present invention, the hydrophobic polymer according to the invention also comprises copolymers (random, block, grafted, in comb arrangement or alternating), besides homopolymers.

In particular, the invention relates to di-, tri- or multiblock polymers comprising at least one block comprising at least one monomer unit according to the invention, namely having a carbonyl group as defined above, as well as at least one other block that can be selected from various types of biocompatible blocks, which for convenience will be called additional blocks hereinafter.

By definition, these additional blocks do not necessarily comprise a monomeric unit possessing a carbonyl group having an H in the α position. Among the latter, we may mention the following polymer blocks:
poly(ethylene glycol), poly(propylene glycol) or poloxamer.

According to a variant of the invention, the additional block is a poly(ethylene glycol) or PEG block of formula $H(OCH_2CH_2)_pOH$, where p varies from 10 to 600.

Polymer According to the Invention

In the context of the present invention, the polymers according to the invention can have a number-average molecular weight between 1000 and 500 000, notably between 5000 and 100 000 and for example between 10 000 and 50 000.

The complexing agent used in the context of the present invention has at least one carboxylic acid function. In this connection, we may notably mention diethylene triamine pentaacetic acid (DTPA), tetraazacyclododacane tetraacetic acid (DOTA) and tetraazacyclotetradecane tetraacetic acid (TETA).

The paramagnetic ion suitable for the present invention is a multivalent paramagnetic metal including, but not limited to the lanthanides and to the transition metals such as iron, manganese, chromium, cobalt and nickel.

Preferably, said paramagnetic ion is a lanthanide which is highly paramagnetic and, even more preferably, it is a gadolinium(III) ion.

According to a first variant, the chelating ligand can be grafted directly on the polymer.

According to a second variant, grafting can be effected on a linker binding the polymer and the chelating agent. Among the linkers that can be used in the context of the present invention, we may notably mention derivatives containing at least two functions capable of reacting with the carbanion and the acyl chloride of the complexing agent. We may mention for example alcohol, amine or thiol functions for reacting on the complexing agent and halide or acid halide functions for reacting on the carbanion.

Method of Grafting the Chelating Ligand of a Paramagnetic Ion

The method of preparation generally consists of functionalizing the main polymer chain by anionic activation with a non-nucleophilic base.

More particularly, the method of preparing the polymer according to the invention can comprise (i) at least one step of activation of a hydrophobic polymer comprising at least one monomer unit possessing at least one carbonyl group and comprising a hydrogen atom in the α position of said at least one carbonyl group, to form a polymer chain having at least one monomer unit bearing a carbanion by elimination of the proton located on the carbon in the α position of said at least one carbonyl group, (ii) at least one step of grafting on said polymer having at least one monomer unit bearing a carbanion with a chelating ligand of a paramagnetic ion, and (iii) at least one step of complexation of the paramagnetic ion with the chelating agent, for example by dissolution of the polymer obtained in the preceding step in a solvent comprising at least one paramagnetic ion.

The general scheme, starting from the starting polymers defined above, comprising respectively monomer units of formula (I) or (II), can be represented according to the following scheme 1:

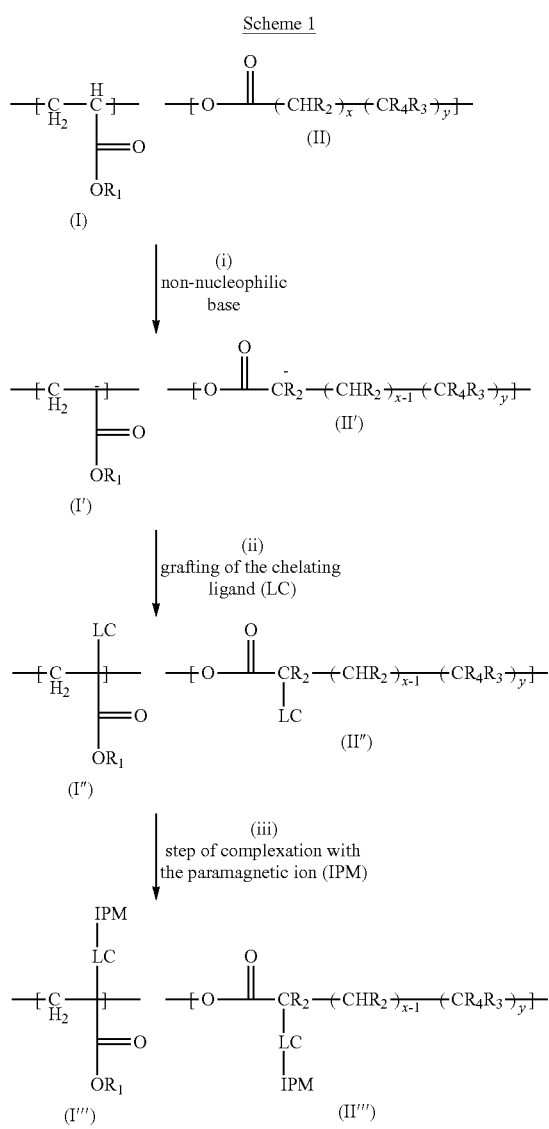

The first step (i) of activation can be obtained by using a strong base such as lithium diisopropylamide (LDA) for example in an anhydrous organic medium. Intermediates such as carbanions and/or enolates are obtained on the main polymer chain. These intermediates are called carbanions hereinafter, for example of formula (I') or (II') according to the above scheme (I).

This first step (i) can be applied in the same way, whether the ester function is located on the main polymer chain or on side chains, as is clear from the above description.

Typically, the first step (i) of the reaction described above can take from 5 to 60 minutes, for example from 15 to 45 minutes.

The reaction according to this first step (i) can be carried out at temperatures in the range from −70 to 30° C., for example from −60 to 0° C.

This first step (i) of preparation of the polymer according to the invention can notably be carried out according to the procedures described in the article "*A Novel Route to Poly(ε-caprolactone) Based Copolymers Via Anionic Derivativation*", S. Ponsart et al., Biomacromolecules 2000, 1, 275-281.

It is to be understood that the degree or extent of substitution of the polymer by the chelating ligand is heavily dependent on this 1st step (i). In particular, the amount of strong base introduced has an influence on this degree of substitution. However, the latter reaches a ceiling at a certain value depending on the starting polymer, even when the strong base is introduced in excess.

Similarly, the reaction temperature of this first step (i) also has an influence on said degree of substitution. The more the reaction temperature is increased, the more the degree of substitution also increases, while remaining below the ceiling value mentioned above.

Other parameters can also affect the degree of substitution, notably the nature of the base and the reaction time.

According to the second step (ii), we proceed with grafting of the complexing agent on the polymer comprising at least one polymer unit in the form of carbanion.

This complexing agent can have been modified chemically beforehand so as to obtain a product that is soluble in the same solvent as the polymer and has a reactive function for grafting.

According to this method, grafting can then be obtained between the polymer comprising at least the polymer unit in the form of carbanion. Grafting can for example be carried out in a solvent such as tetrahydrofuran, toluene, aromatic derivatives of benzene, dioxane and generally any solvent that does not react with the base selected for the reaction or the carbanion at a temperature between −70 and 30° C., for example at −40° C., for between 5 and 60 minutes, for example for 30 minutes.

According to the third step (iii), the polymer according to the present invention can finally be obtained by reaction of the product obtained according to the preceding step in a solvent such as DMSO or a mixture of solvents for example water/acetone containing a paramagnetic ion, for example gadolinium trichloride, and stirring for between 1 hour and 10 days, for example 2 days, for example at room temperature.

The polymer obtained at the end of this process has the characteristic of being hydrophobic and insoluble in aqueous solvents, for example biological fluids. This polymer thus obtained has substituents (complexing agent+paramagnetic ion) on its chain that make it visible in MRI.

In general, the degree of substitution of the chelating agent varies from 0.01 to 40%.

More particularly, the degree of substitution that can be obtained when the polymer comprises at least one carbonyl group in the main polymer chain can range from 0.01 to 10%, for example can be less than 10%.

Moreover, the degree of substitution can be between 0.01 and 40%, for example can be less than 30% when at least one carbonyl group is located outside the main polymer chain, in other words is contained in a side chain to the main polymer chain.

Medical Device

The present invention covers a medical device comprising at least one polymer according to the present invention.

The polymer according to the present invention can form an integral part of the medical device per se; it is in other words comprised in its bulk or else is located on the surface of said device in the form of a coating of a thickness such as to make the medical device visible in magnetic resonance imaging.

Typically, the coating can form a thickness between 1 and 1000 μm, for example between 10 and 100 μm.

In the variant consisting of coating the medical device, various methods can be used that are known per se by a person skilled in the art. In this connection, we may mention electrospinning, dipping, application of spray drying or aerography or spraying.

Of course, the present application extends to medical devices that have undergone some other type of bulk and/or surface treatment of a kind different from that considered in the present invention. As examples, we may mention bacterial and fungal antiadhesion treatments, treatments permitting release of active principles such as antibiotics, antibacterials, antifungals, anti-inflammatories, and all kinds of active principles that can be released in situ.

As medical devices that are particularly suitable for the present invention, we may mention medical devices more particularly finding application in the field of gynecology for example for mesh or prostheses for genital prolapse.

According to another aspect, the present invention extends to a method of marking a medical device, characterized in that it comprises at least one step of depositing a polymer according to the invention on the surface of the material, notably on a target zone of the medical device.

According to this aspect, the polymer according to the invention is thus deposited on prostheses, notably in the form of an inscription so that postoperative monitoring can be carried out based on direct marking on the material.

More particularly, the marking can be intended for traceability of the medical device. The medical device can thus be identified throughout its life, whether during manufacture, distribution or once in position. Thus, the marking can assume any form or surface on the medical device.

Even more particularly, the inscriptions can take the form of numerals, of letters or of any other type of characters useful for traceability.

As examples, marking can be carried out according to one of the following methods:

- deposition of a homogeneous surface of polymer according to the invention on the surface of the material, in which the characters are inscribed.

CE 1899

- deposition of characters on the surface of the material by techniques of micro-printing, in which the polymer according to the invention represents the ink.

CE 1899

This aspect of the invention is particularly advantageous in that the marking is thus integral with the medical device rather than with the packaging thereof as is usually the case.

The invention also extends to a medical device provided with marking produced by means of a polymer according to the present invention.

The polymer according to the present invention can also find application in any field of medicine where MRI is used.

These various fields can be classified by surgical specialties or by type of materials, notably implantable which are used in several fields of medicine.

Classification by Medico-Surgical Specialties:

Gynecology:
supporting mesh in the treatment of genitourinary and rectal prolapse (vaginal and abdominal surgery)
clips for tubal sterilization
devices for tubal obstruction by the endoluminal route
ring for cervical cerclage
intraperitoneal and endouterine antiadhesion devices Urology:
artificial urinary sphincter
penile prosthesis
patch for reinforcement of the corpora cavernosa (treatment of curvature of the penis, Lapeyronie disease)
periurethral balloons
periurethral injectable devices
suburethral bands
endourethral stents, prostheses
urinary bypass catheters (transcutaneous and natural routes).

Orthopedics:
synthetic ligaments
neo cartilage or joint
synthetic intervertebral discs
femoral head
acetabulum (femur and humerus)
tibial plateau
humeral head.

ORL:
cochlear implants
internal ear prostheses, osseous substitutes. Endocrinology:
implantable pumps.

Vascular:
endovascular prostheses
arterial and venous prostheses
devices for closure and hemostasis, transarterial vascular access
cases and catheters of chambers, implantable vascular access.

Neurology:
vascular stents
devices for occlusion of aneurysm and arterial vascular dissection
electrostimulation probes
patches and reinforcements of dura mater and meninges.

Ophthalmology:
synthetic corneas.

Digestive Tract Surgery:
hernia reinforcing plates (mesh) (diaphragm, parietal, inguinal, crural)
gastric bands
splenic threads
esophageal prostheses
stents for biliary tract and digestive tract (small intestine, colon, rectum) endoprosthesis
tubes for parenteral nutrition
artificial anal sphincter.

Cardiology:
coronary stents
pacemaker cases and tubes
systolic pacing catheters

Radiology:

agents for vascular embolization, for vascular occlusion (arterial or venous) (temporary or permanent).

Implantable Materials Used in Several Medical Fields:

Surgical suture threads.

Venous and arterial catheters (central and peripheral).

Intracorporeal thermal probes.

Surgical drains, tubular and plates, drainage channels.

Synthetic clamps for approximation, locating, for digestive anastomosis and prosthesis fixation.

Tissue engineering: Matrix for supporting stem cells in reconstructive surgery.

The polymer according to the invention can, finally, find application in the actual enclosure of the MRI equipment.

The work environment in the MRI room requires absence of metals capable of disturbing the magnetic field of the MRI. This environment notably requires the development of metal-free, MRI-compatible equipment for ventilation and resuscitation. We may mention in this connection the following equipment: table, headrest, neck brace, splint, staples, supports and holds for positioning and locating in MRI.

The examples given below illustrate the invention without limiting its scope.

EXAMPLES

Example 1

Preparation Based on a Poly ε-caprolactone Polymer

Characterization of the products is illustrated by the accompanying drawings.

The synthesis scheme is as follows:

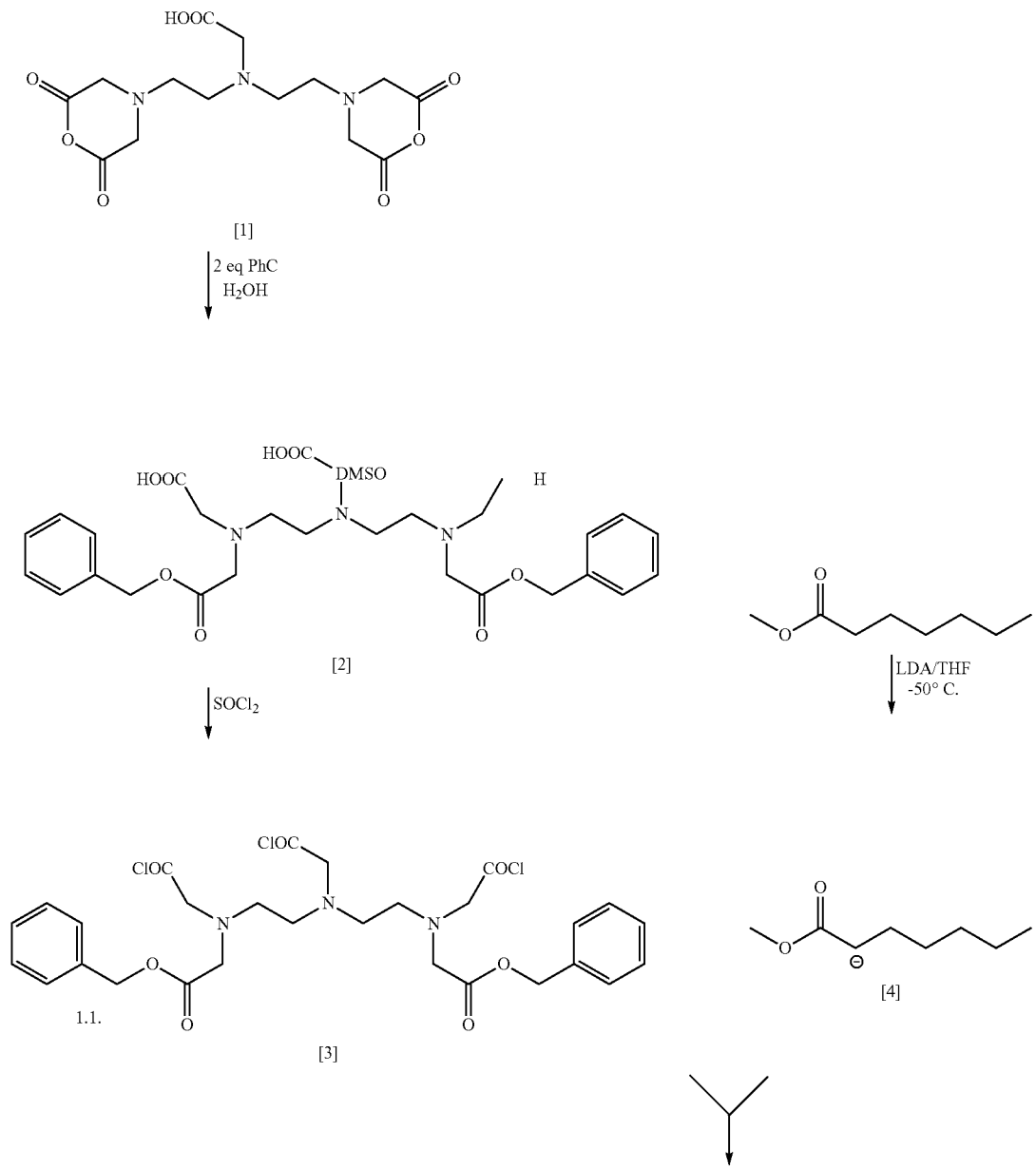

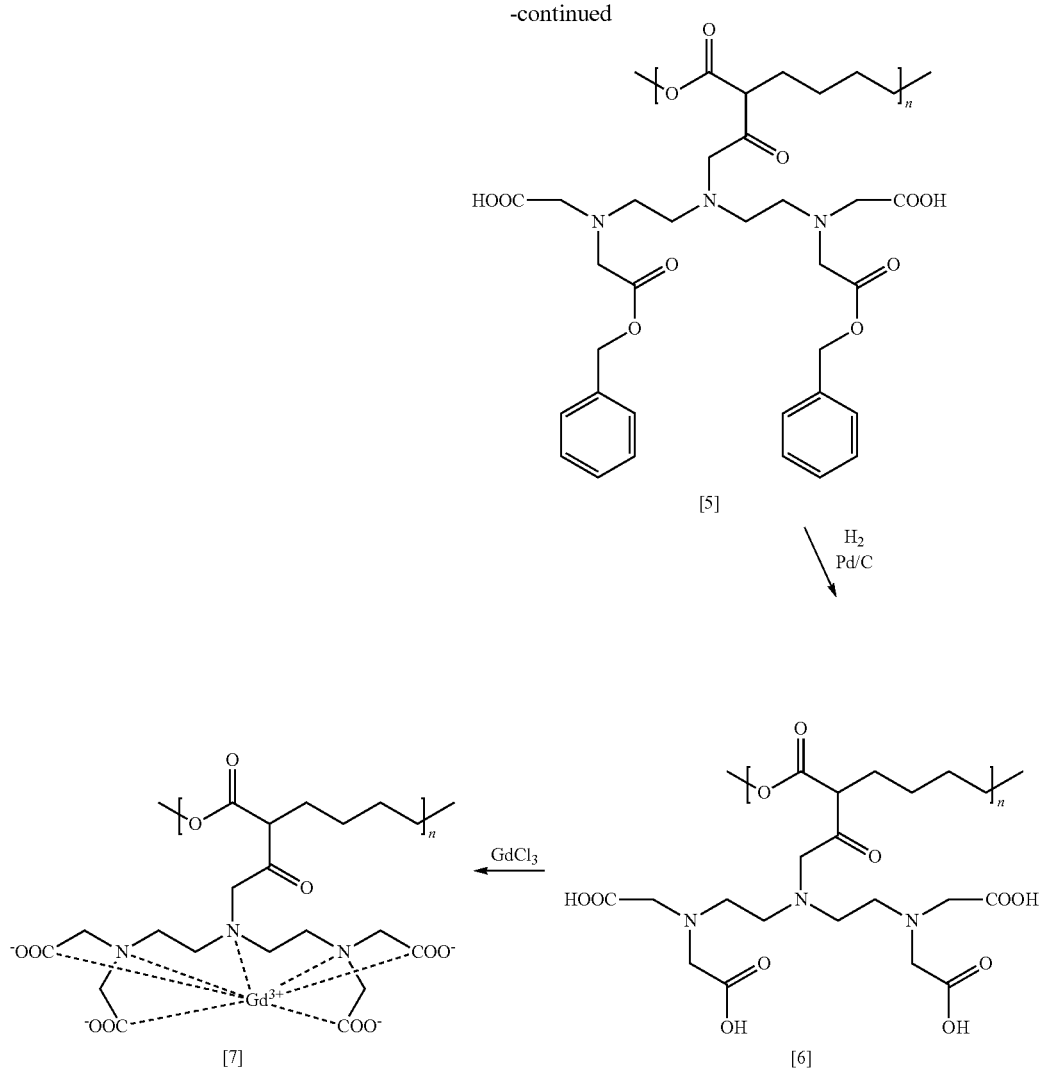

[5], [6], [7]

Synthesis of Diphenylated DTPA [2] (M=550 g/mol)

730 μl of benzyl alcohol (2.5 eq.) is added to a suspension of 1 g of DTPA dianhydride [1] in DMSO (insoluble at room temperature). The mixture is left at room temperature for 5 hours, and development of the reaction is monitored by infrared spectrometry (disappearance of the peak characteristic of the dianhydride at 1800 cm$^{-1}$).

Treatment:

The excess DMSO and benzyl alcohol are evaporated for 2 days by means of a vane pump. The product obtained is recrystallized from ethyl ether. A white powder is recovered.

Figure 1:
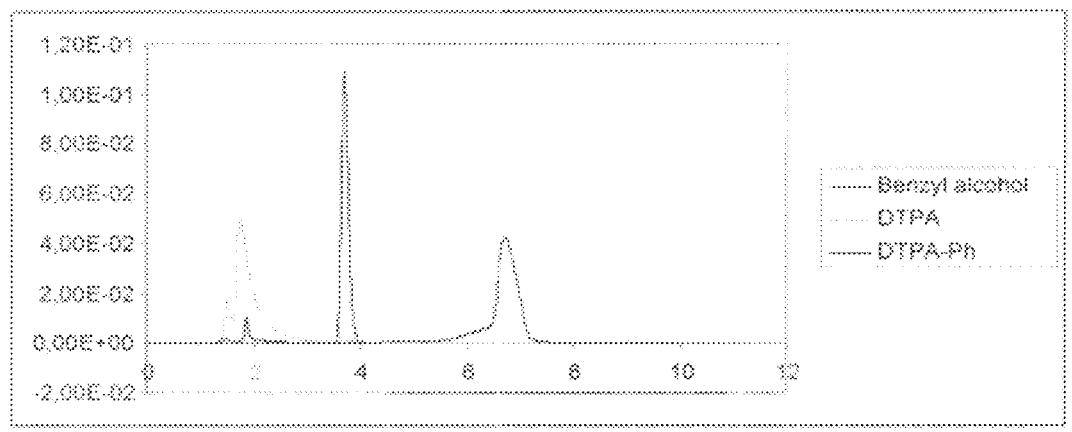

Characterization:

HPLC: Use of HPLC in isocratic mode with H$_2$O/acetonitrile (65/35) mixture as eluent, detection by UV at a wavelength of 257 nm, revealing the presence of a new structure (diphenylated DTPA). FIG. 1 shows the chromatograms obtained by HPLC in isocratic mode with a 65/35 ratio H$_2$O/ACN, DTPA-Ph, benzyl alcohol and DTPA.

Figure 2:
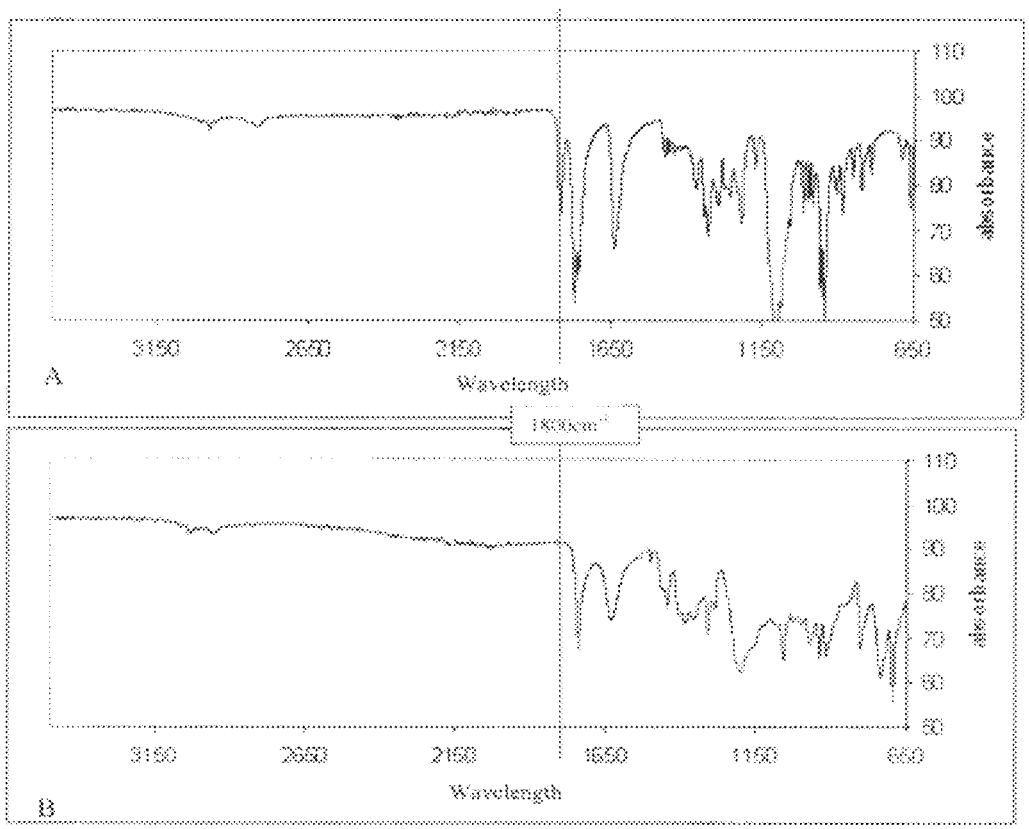

Retention time (diphenylated DTPA)=6.75 min
Retention time (benzyl alcohol)=3.7 min
Retention time (DTPA)=1.9 min Infrared spectrometry: Infrared analysis reveals disappearance of the peak characteristic of the anhydride, at 1800 cm$^{-1}$. FIG. 2 shows the infrared spectra of DTPA dianhydride (A) and diphenylated DTPA (B).

1H Nuclear magnetic resonance (DMSO D6): Proton NMR provides information on the structure of the product and on the presence of two aromatic groups on the DTPA.

2.9 ppm (m, 8H, H1), 3.4 ppm (m, 6H, H2), 3.6 ppm (m, 4H, H4) 5.1 ppm (m, 2H, H5), 7.3 ppm (m, 10H, aromatic H6)

In comparison with benzyl alcohol:

Alcohol: 4.3 ppm (d, CH2); 5.2 ppm (t, OH); 7.15 ppm (aromatic)

1.2. Synthesis of DTPA-diPH-Cl [3]

1 g of diphenylated DTPA is dissolved in 8 ml of SOCl$_2$. The mixture is left at room temperature for 2 hours, a dark brown oil is recovered after evaporation of the excess SOCl$_2$, then dissolved in THF. The raw product is used directly in the next step.

1.3. Synthesis of PCL-DTPA-diPh [5]

2 g of PCL is dissolved in 200 ml of THF at −40° C., 17.5 ml of a 2N solution of LDA (lithium diisopropylamine) (2 eq.) is added dropwise with stirring. The reaction is continued for 30 minutes at −40° C. and makes it possible to obtain the carbanion of PCL [4]. DTPA-diPH-Cl is diluted in 20 ml of THF then added dropwise to the carbanion in 30 minutes, at −40° C.

Treatments:

It is neutralized with 150 ml of $H_2O$/HCl to pH 4-5, which is followed by liquid extraction 3 times with dichloromethane, then washing of the organic phase with water and finally decanting, recovery of the organic phase which evaporated. The product obtained is precipitated in MeOH and then filtered.

Figure 3:
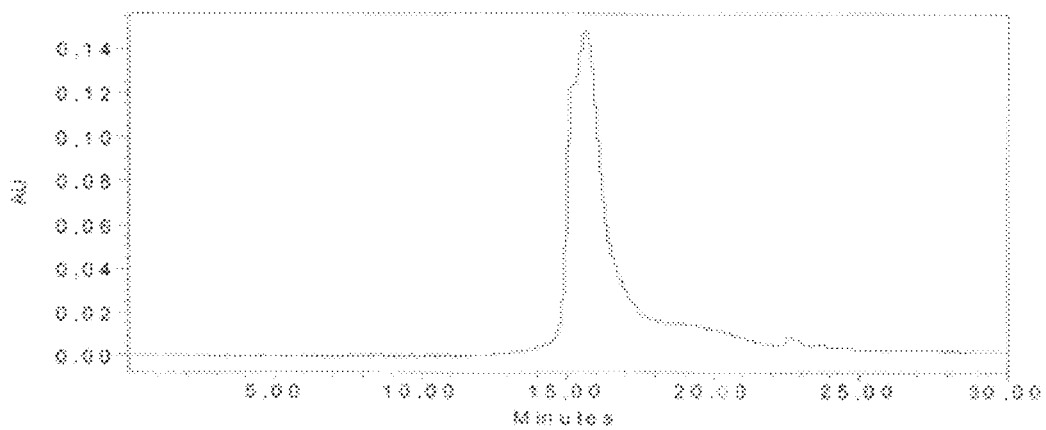

Characterization:

Size exclusion chromatography (SEC): The detector used for SEC is a UV-Visible detector with diode arrays (PDA). SEC shows the presence of a polymer absorbing at a wavelength of 292 nm. As PCL does not absorb at this wavelength, this new product corresponds to modified PCL which corresponds to PCL-diphenylated DTPA. FIG. 3 shows the chromatogram at λ=292 nm of the PCL-DTPA-diPh obtained by size exclusion chromatography coupled to a diode array detector.

1H NMR: Proton NMR reveals the substitution and makes it possible to measure the degree of grafting of DTPA on PCL. Comparison of the ratios of intensity of the integrations of the aromatic protons and of the protons of the caprolactone unit of PCL gives the degree of substitution, which is close to 2%.

4.0 ppm (t, $CH_2$—O); 2.2 ppm (t, $CH_2$—CO—O); 1.5 ppm (m, 2 $CH_2$ in gamma and epsilon); 1.3 ppm (m, $CH_2$ center); 5.1 ppm ($CH_2$ aromatic).

Acid-basic assay: This consists of determining the carboxylic acid functions present on the grafted DTPA and therefore makes it possible to determine the degree of substitution on PCL.

This assay shows that PCL was substituted to 2.5% by the diphenylated DTPA.

1.4. Synthesis of PCL-DTPA [6]

This step consists of deprotection of the DTPA grafted on the polymer by debenzylation.

PCL-DTPA-Ph (1 g) is dissolved in 80 ml of THF. 50 mg of a 10% suspension of Pd/C is added to the solution. The mixture is left at a pressure of 4 bar of $H_2$ for 3 days at RT.

Treatment:

After filtration and then evaporation of the THF, the polymer is reprecipitated in methanol.

Characterization:

SEC with PDA detector: The chromatogram of the polymer obtained shows that the polymer no longer contains aromatics and that the benzyl alcohol has been removed.

$^1$H NMR: On the NMR spectrum we observe, relative to PCL-diphenylated DTPA, disappearance of the peaks corresponding to the aromatic protons.

1.5. Synthesis of PCL-DTPA-Gd [7]

100 mg of the modified polymer is dissolved in DMSO, and mixed with 30 mg of a solution of $GdCl_3$ (10 eq. relative to the grafted DTPA) in 10 ml of DMSO. The mixture is stirred at room temperature for two days to complete the complexation.

Treatment:

Evaporation of DMSO, and $CH_2Cl_2$/$H_2O$ extraction. Evaporation of $CH_2Cl_2$ and reprecipitation in MeOH.

Characterization:

Relaxation Time of the Protons of PCL:

The results given below correspond to the relaxation time of the protons of the PCL chain, substituted or not. They show the presence of the $Gd^{3+}$ ion in PCL-DTPA-Gd

| shift | relaxation time (ms) | |
| --- | --- | --- |
| chemical | PCL | PCL-DTPA-Gd |
| 4.00 ppm | 693.43 | 480.78 |
| 2.28 | 693.06 | 525.93 |
| 1.54 | 632.62 | 456.00 |
| 1.31 | 671.10 | 475.15 |

MRI: After analysis of the accompanying images shown in FIG. 4, the No. 3 well corresponding to PCL-DTPA-Gd substituted at 2% gives a significant positive signal. In comparison, the No. 12 well corresponding to PCL mixed with Magnevist (commercial MRI contrast product) also gives a significant positive signal. FIG. 4 shows the MRI images of the various grafted polymers and of the negative and positive MRI controls (3 tesla). FIG. 4 also shows various grafted polymers with different degrees of substitution and different methods of complexation (FIG. 4-A; Sequence 2D weighted T2) negative controls (8-11) and positive controls (12) (FIG. 4-B; Sequence 2D weighted T1).

Example 2

Method of Spraying for Producing a Coating that is Visible in MRI

In order to provide a medical device of the mesh type with a character of visibility in MRI, a method of spraying by means of an aerograph was developed for this application (Infinity® aerograph made by Harder & Steenbeck equipped with a 0.15 mm nozzle and a 5 mL cup).

For this, it is necessary to dissolve the polymer in an easily volatilizable organic solvent (such as acetone, chloroform, dichloromethane etc.). The concentration of polymer in the solvent must be between 1 and 5% (weight by volume) in order to obtain a clear solution that can be sprayed easily, uniformly and continuously.

The solution of polymer is sprayed under pressure at 2.5 bar at a distance of 5 cm from the mesh directly on its surface, either localized or on the whole surface. A deposit of 20 to 50 µm of polymer on the surface of the implant is necessary to permit MRI visualization of the latter, while preserving the intrinsic properties of the implant.

The mesh is dried for 12 hours under vacuum for complete evaporation of the solvent. The amount of polymer deposited on the implant is determined by comparing the weight of the implant before and after spraying.

Contact Angle

The contact angle is measured according to the protocol described above.

Slide alone: 31°
Slide containing PCL-DTPA-Gd: 80°
Slide containing PCL: 82°

This test clearly shows that the polymer obtained is hydrophobic.

Degradation Test

A defined amount of substituted polymer is deposited in 30 tubes, for example 50 mg per tube, to which 5 ml of PBS is added. The tubes are then put in a stove at 37° C. with stirring to simulate physiological conditions.

3 tubes correspond to a degradation time:

|         |
|---------|
| 7 days  |
| 15 days |
| 30 days |
| 60 days |
| 90 days |
| 150 days |
| 210 days |
| 270 days |
| 330 days |
| 400 days |

Each sample is then filtered and analyzed by size exclusion chromatography. The number-average molecular weights and the molecular weights at the top of the peak of each sample are compared, to trace the degradation relative to the initial molecular weights of the starting polymer.

Figure 5:
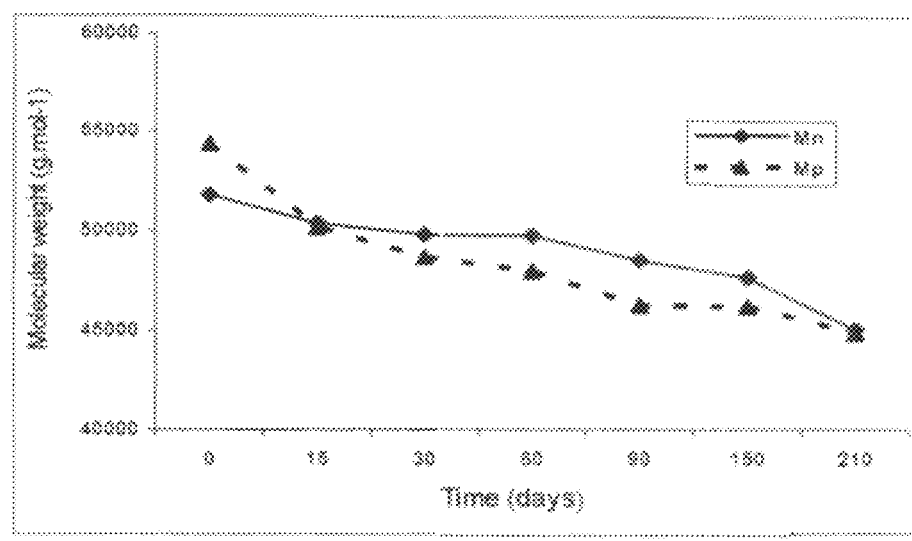

FIG. 5 shows the variation of the number-average molecular weights (Mn) and molecular weights at the top of the peak (Mp) for 210 days. Regardless of the type of molecular weight, a notable decrease in molecular weights is observed (about 20% in 210 days).

Visualization of the Mesh in vitro

The mesh is visualized using the equipment 7T Bruker DRX300SWB Imager, "mini-imaging" configuration (gradient 144 mT/m, bird-cage resonator 64 mm).

Figure 6:
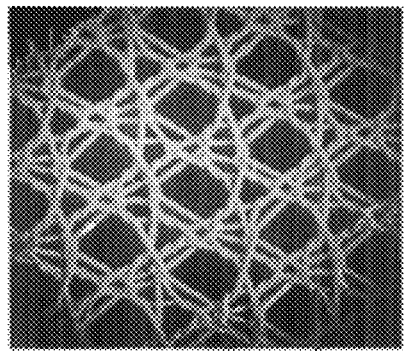
Figure 6:
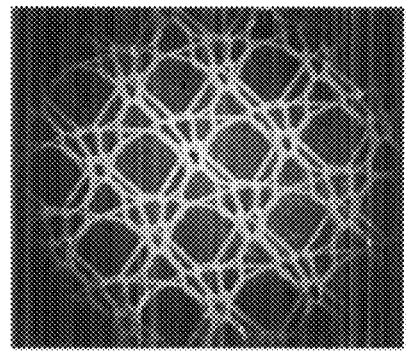
Figure 6:
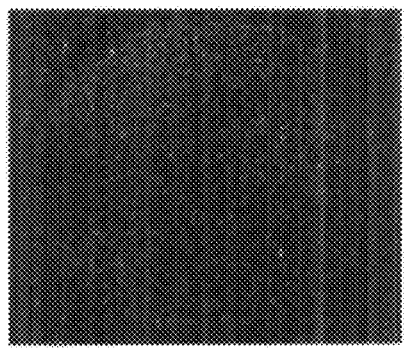
Figure 6:
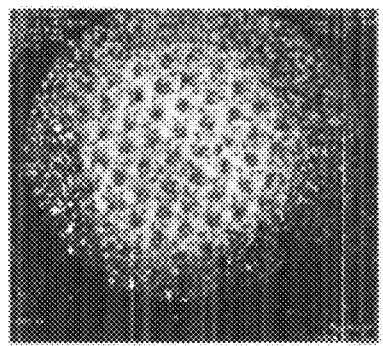

FIG. 6 shows (i) the mesh as negative control with respect to the two images on the left, namely a mesh coated with PCL-DTPA without gadolinium and (ii) the sample coated with PCL-DTPA-Gd as prepared in example 1 with respect to the two images on the right.

Moreover, this FIG. 6 is made up as follows:

a/ Mesh with a coating, seen in the optical microscope (magnification ×20).

b/ MRI analysis in echoes of spin 2D with inversion unit, therefore weighted sequence T2 sensitized T1.

Visualization of the Mesh in vivo

Figure 7:
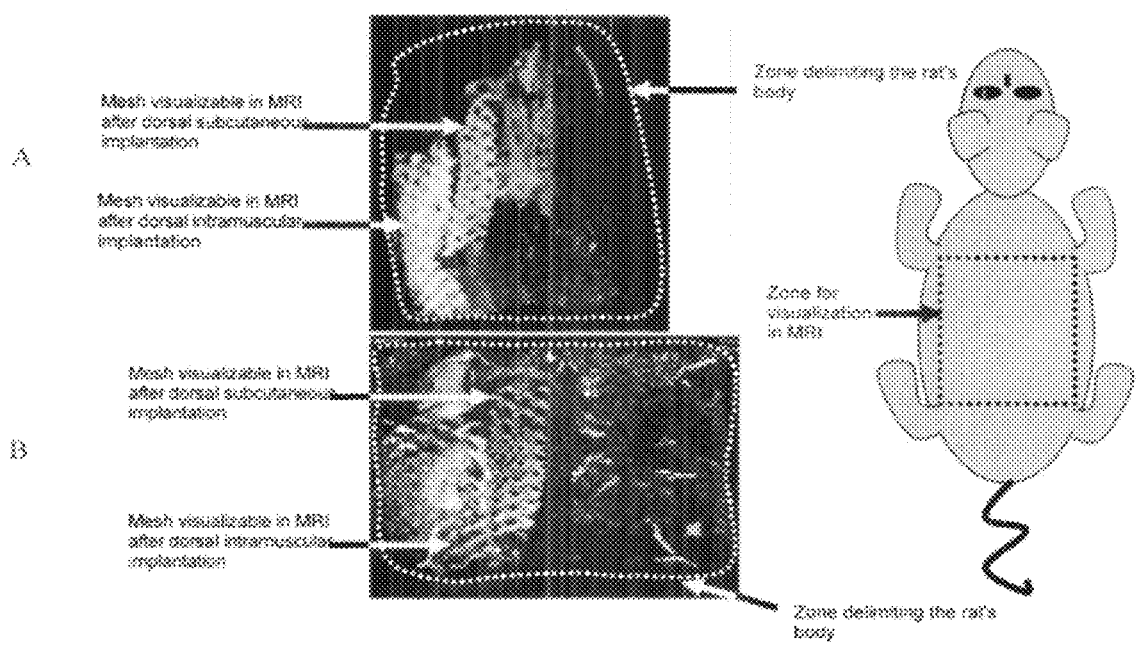

A rat underwent dorsal implantation of 4 prostheses (1×3 cm) of the mesh type (2 covered with polymers visible in MRI and 2 covered with polymers not visible in MRI). The implants were subcutaneous and intramuscular. The mesh is visualized with the equipment 7T Bruker DRX300SWB Imager, "mini-imaging" configuration (gradient 144 mT/m, surface-antenna resonator 1H/31P). FIG. 7 shows the rat in echo sequence of gradient 3D (A) and in echo sequence of gradient 3D of the FLASH type with variable flip angles (VFA) (B).

These photographs demonstrate that the meshes can be visualized well, 3 weeks after implantation.

The invention claimed is:

1. A hydrophobic polymer, comprising a monomer unit on which a chelating ligand complexed with a paramagnetic ion is grafted, comprising a polymer that is a polyacrylate comprising identical or different monomer units of formula (I):

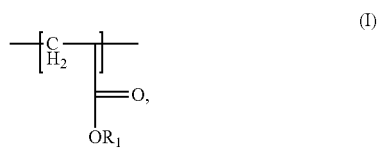

wherein:
$R_1$ represents a $(C_1-C_{12})$alkyl group or a $(C_1-C_8)$cycloalkyl group optionally substituted with a $(C_1-C_4)$alkyl group; or a polymer that is a polyester comprising identical or different monomer units of formula (II):

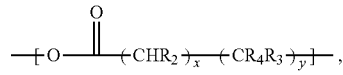

wherein:
$R_2$, $R_3$ and $R_4$ independently represent a hydrogen atom, a $(C_1-C_{12})$ alkyl group or a $(C_1-C_8)$ cycloalkyl group optionally substituted with a $(C_1-C_{12})$ alkyl group;
x represents an integer between 0 and 12; and
y represents an integer between 0 and 8,
such that x and y are not zero simultaneously,
wherein:
the chelating ligand is grafted on a carbon atom at the α position of a carbonyl group in formula (I) or formula (II).

2. The polymer of claim 1, wherein the monomer units in formula (I) or formula (2) comprise from 2 to 12 carbon atoms.

3. The polymer of claim 1, wherein the monomer unit comprises 2 to 7 carbon atoms.

4. The polymer of claim 1, wherein the monomer units are located outside a main polymer chain or alternatively in the main polymer chain.

5. The polymer of claim 1, wherein the polymer is a polyacrylate comprising identical or different monomer units of formula (I).

6. The polymer of claim 5, wherein the identical or different monomeric units of formula (I) are at least one monomer selected from the group consisting of butyl acrylate, 2-ethylhexyl acrylate, methyl acrylate and ethyl acrylate.

7. The polymer of claim 1, wherein the polymer is a polyester comprising identical or different monomer units of formula (II).

8. The polymer of claim 7, wherein x represents an integer between 0 and 6.

9. The polymer of claim 7, wherein y represents an integer between 0 and 6.

10. The polymer of claim 1, wherein the polymer is comprises polymerized monomers of at least one monomer selected from the group consisting of hydroxybutyric acid, hydroxyvaleric acid, hydroxyhexanoic acid, hydroxyoctanoic acid, δ-valerolactone, γ-butyrolactone, ε-decalactone, pivalolactone, diethylpropiolactone, glycolic acid, p-dioxanone (1,4-dioxan-2-one), 1,4-dioxepan-2-one, 1,4-dioxepan-5-one, 1,5-dioxepan-2-one, 6,6-dimethyl-1,4-dioxan-2-one, 2,5-diketomorpholine, 3-methyl-1,4-dioxane-2,5-dione, 3,3-diethyl-1,4-dioxan-2,5-dione, 6,6-dimethyldioxepan-2-one and mixtures thereof.

11. The polymer of claim 1, wherein the polymer is comprises poly(Σ-caprolactone).

12. The polymer of claim 1, wherein the polymer is a homopolymer, or a copolymer.

13. The polymer of claim 1 having a number-average molecular weight between 1000 and 500 000.

14. The polymer of claim 1 having a number-average molecular weight between 5000 and 100 000.

15. The polymer of claim 1, wherein the chelating ligand comprises at least one carboxylic acid function selected from the group consisting of diethylene triamine pentaacetic acid (DTPA), tetraazacyclododacane tetraacetic acid (DOTA) and tetraazacyclotetradecane tetraacetic acid (TETA).

16. The polymer of claim 1, wherein a degree of substitution of the chelating ligand varies from 0.01 to 40%.

17. The polymer of claim 1, wherein a degree of substitution of the chelating ligand varies from 0.01 to 10%.

18. A medical device, comprising the polymer of claim 1.

19. A method of preparing the polymer of claim 1, the method comprising:

activating a hydrophobic polymer comprising a monomer unit comprising a carbonyl group and a hydrogen atom at an $\alpha$ position of the carbonyl group, to form an anionic polymer chain having at least one monomer unit bearing a carbanion by elimination of a proton on the carbon in the $\alpha$ position of the carbonyl group;

(ii) grafting the chelating ligand onto the anionic polymer chain and (iii) complexing the paramagnetic ion with the chelating ligand.

20. A method of preparing a medical device, the method comprising coating with the polymer of claim 1 in a solution comprising the polymer.

21. A method of marking, the method comprising depositing the polymer of claim 1 onto a surface of a material.

* * * * *